United States Patent
Gaudiani

(10) Patent No.: US 8,634,935 B2
(45) Date of Patent: Jan. 21, 2014

(54) TRANSCORONARY SINUS PACING SYSTEM, LV SUMMIT PACING, EARLY MITRAL CLOSURE PACING, AND METHODS THEREFOR

(76) Inventor: Vincent A. Gaudiani, Redwood City, CA (US)

( * ) Notice: Subject to any disclaimer, the term of this patent is extended or adjusted under 35 U.S.C. 154(b) by 0 days.

(21) Appl. No.: 13/278,089

(22) Filed: Oct. 20, 2011

(65) Prior Publication Data

US 2012/0041530 A1 Feb. 16, 2012

Related U.S. Application Data

(63) Continuation of application No. 11/770,371, filed on Jun. 28, 2007, now Pat. No. 8,068,920.

(60) Provisional application No. 60/828,708, filed on Oct. 9, 2006, provisional application No. 60/827,967, filed on Oct. 3, 2006.

(51) Int. Cl.
*A61N 1/362* (2006.01)

(52) U.S. Cl.
USPC .......................................... 607/116; 607/119

(58) Field of Classification Search
USPC .......................................................... 607/116
See application file for complete search history.

(56) References Cited

U.S. PATENT DOCUMENTS

| | | | |
|---|---|---|---|
| 4,917,102 A | 4/1990 | Miller et al. |
| 5,477,864 A | 12/1995 | Davidson |
| 5,549,109 A | 8/1996 | Samson et al. |
| 5,662,109 A | 9/1997 | Hutson |
| 5,919,213 A | 7/1999 | Nelson et al. |
| 5,944,746 A | 8/1999 | Kroll |
| 5,957,956 A | 9/1999 | Kroll et al. |
| 6,027,476 A | 2/2000 | Sterman et al. |
| 6,067,471 A | 5/2000 | Warren |
| 6,094,597 A | 7/2000 | Wold |
| 6,152,141 A | 11/2000 | Stevens et al. |

(Continued)

FOREIGN PATENT DOCUMENTS

| | | |
|---|---|---|
| WO | WO 03/086502 A2 | 10/2003 |
| WO | WO 03/086502 A3 | 4/2004 |

OTHER PUBLICATIONS

InSync Sentry and InSync Maximo. Available at: www.medtronic.com. Accessed Jan. 8, 2008.

(Continued)

*Primary Examiner* — Christopher D Koharski
*Assistant Examiner* — Natasha Patel
(74) *Attorney, Agent, or Firm* — Wilson Sonsini Goodrich & Rosati

(57) ABSTRACT

A transcoronary sinus pacing system comprising a sheath having a lumen, a pacing catheter having a pacing needle, wherein the catheter can be advanced within the lumen and placed in the LV summit, and a right ventricular pacing device. A LV summit pacing device. An early mitral valve closure pacing device configured to operate with a right ventricular apex pacing device. A method for implanting a pacing device at a target coronary sinus tissue location, wherein the target can be the posterior LV summit. A method for achieving early closure of a mitral valve. A method for using visualization devices such as fluoroscopy or ultrasound and/or catheter features such as a radiopaque marker to locate a target location for LV pacing and to avoid piercing an artery or the pericardium when anchoring the LV pacing electrode.

12 Claims, 18 Drawing Sheets

(56) References Cited

U.S. PATENT DOCUMENTS

| | | | |
|---|---|---|---|
| 6,275,734 B1 | 8/2001 | McClure et al. |
| 6,282,444 B1 | 8/2001 | Kroll et al. |
| 6,356,791 B1 | 3/2002 | Westlund et al. |
| 6,363,280 B1 | 3/2002 | Mouchawar et al. |
| 6,377,852 B1 | 4/2002 | Bornzin et al. |
| 6,493,591 B1 | 12/2002 | Stokes |
| 6,567,697 B1 | 5/2003 | Kroll et al. |
| 6,574,505 B1 | 6/2003 | Warren |
| 6,625,489 B2 | 9/2003 | Sheth et al. |
| 6,633,780 B1 | 10/2003 | Berger |
| 6,671,560 B2 | 12/2003 | Westlund et al. |
| 6,675,042 B2 | 1/2004 | Swerdlow et al. |
| 6,701,187 B1 | 3/2004 | Bornzin et al. |
| 6,723,069 B1 | 4/2004 | Weldon et al. |
| 6,723,082 B1 | 4/2004 | Payne et al. |
| 6,728,563 B2 | 4/2004 | Rashidi |
| 6,733,499 B2 | 5/2004 | Scheib |
| 6,733,500 B2 | 5/2004 | Kelley et al. |
| 6,736,782 B2 | 5/2004 | Pfeiffer et al. |
| 6,741,878 B2 | 5/2004 | Fuimaono et al. |
| 6,746,431 B2 | 6/2004 | Pfeiffer et al. |
| 6,748,255 B2 | 6/2004 | Fuimaono et al. |
| 6,775,566 B2 | 8/2004 | Nissilä |
| 6,782,291 B1 | 8/2004 | Bornzin et al. |
| 6,788,972 B2 | 9/2004 | Prutchi et al. |
| 6,792,316 B2 | 9/2004 | Sass |
| 6,792,318 B2 | 9/2004 | Chitre et al. |
| 6,804,553 B2 | 10/2004 | Zheng et al. |
| 6,807,447 B2 | 10/2004 | Griffin, III |
| 6,821,265 B1 | 11/2004 | Bertolero et al. |
| 6,823,215 B2 | 11/2004 | Obel et al. |
| 6,826,421 B1 | 11/2004 | Beatty et al. |
| 6,830,568 B1 | 12/2004 | Kesten et al. |
| 6,835,188 B2 | 12/2004 | Samson et al. |
| 6,837,864 B1 | 1/2005 | Bertolero et al. |
| 6,839,588 B1 | 1/2005 | Rudy |
| 6,849,073 B2 | 2/2005 | Hoey et al. |
| 6,850,800 B1 | 2/2005 | Uhrenius et al. |
| 6,859,667 B2 | 2/2005 | Goode |
| 6,868,291 B1 | 3/2005 | Bonner et al. |
| 6,882,886 B1 | 4/2005 | Witte et al. |
| 6,889,093 B1 | 5/2005 | Flammang |
| 6,892,091 B1 | 5/2005 | Ben-Haim et al. |
| 6,901,288 B2 | 5/2005 | Janke et al. |
| 6,901,297 B2 | 5/2005 | Frericks et al. |
| 6,902,545 B2 | 6/2005 | Bertolero et al. |
| 6,904,315 B2 | 6/2005 | Panken et al. |
| 6,907,296 B1 | 6/2005 | Doan et al. |
| 6,907,297 B2 | 6/2005 | Wellman et al. |
| 6,909,916 B2 | 6/2005 | Spinelli et al. |
| 6,909,919 B2 | 6/2005 | Jain et al. |
| 6,916,317 B2 | 7/2005 | Falwell et al. |
| 6,926,669 B1 | 8/2005 | Stewart et al. |
| 6,934,583 B2 | 8/2005 | Weinberg et al. |
| 6,944,506 B1 | 9/2005 | Morgan et al. |
| 6,947,785 B1 | 9/2005 | Beatty et al. |
| 6,950,696 B2 | 9/2005 | Björling et al. |
| 6,960,206 B2 | 11/2005 | Keane |
| 6,961,602 B2 | 11/2005 | Fuimaono et al. |
| 6,961,621 B2 | 11/2005 | Krishnan et al. |
| 6,968,237 B2 | 11/2005 | Doan et al. |
| 6,970,733 B2 | 11/2005 | Willis et al. |
| 6,973,340 B2 | 12/2005 | Fuimaono et al. |
| 6,973,341 B2 | 12/2005 | Watson |
| 6,973,352 B1 | 12/2005 | Tsutsui et al. |
| 6,984,232 B2 | 1/2006 | Vanney et al. |
| 6,986,769 B2 | 1/2006 | Nelson et al. |
| 6,987,996 B2 | 1/2006 | Fuimaono et al. |
| 6,987,999 B1 | 1/2006 | Kroll |
| 6,988,007 B1 | 1/2006 | Morgan et al. |
| 6,999,814 B2 | 2/2006 | Hauser et al. |
| 6,999,821 B2 | 2/2006 | Jenney et al. |
| 7,010,358 B1 | 3/2006 | Kroll et al. |
| 7,027,876 B2 | 4/2006 | Casavant et al. |
| 7,031,773 B1 | 4/2006 | Levine et al. |
| 7,039,450 B2 | 5/2006 | Duarte |
| 7,041,079 B2 | 5/2006 | Yozu et al. |
| 7,047,068 B2 | 5/2006 | Haissaguerre |
| 7,081,114 B2 | 7/2006 | Rashidi |
| 7,085,606 B2 | 8/2006 | Flach et al. |
| 7,089,045 B2 | 8/2006 | Fuimaono et al. |
| 7,089,065 B2 | 8/2006 | Westlund et al. |
| 7,097,641 B1 | 8/2006 | Arless et al. |
| 7,099,712 B2 | 8/2006 | Fuimaono et al. |
| 7,103,409 B2 | 9/2006 | Warren |
| 7,110,827 B2 | 9/2006 | Sage et al. |
| 7,151,963 B2 | 12/2006 | Havel et al. |
| 7,158,825 B1 | 1/2007 | Kroll et al. |
| 7,200,434 B2 | 4/2007 | Havel et al. |
| 7,203,546 B1 | 4/2007 | Kroll et al. |
| 7,203,547 B1 | 4/2007 | Kroll et al. |
| 8,068,920 B2 | 11/2011 | Gaudiani |
| 2002/0077685 A1* | 6/2002 | Sundquist et al. ............ 607/116 |
| 2003/0050670 A1 | 3/2003 | Spinelli et al. |
| 2003/0078645 A1* | 4/2003 | Pigott ........................ 607/122 |
| 2005/0209668 A1* | 9/2005 | Friedman et al. ............ 607/122 |
| 2006/0241465 A1* | 10/2006 | Huennekens et al. ........ 600/458 |

OTHER PUBLICATIONS

International search report dated Jan. 29, 2008 for PCT Application No. US2007/80160.

Office action dated Apr. 21, 2011 for U.S. Appl. No. 11/770,371.

Office action dated Jul. 8, 2007 for U.S. Appl. No. 11/770,371.

* cited by examiner

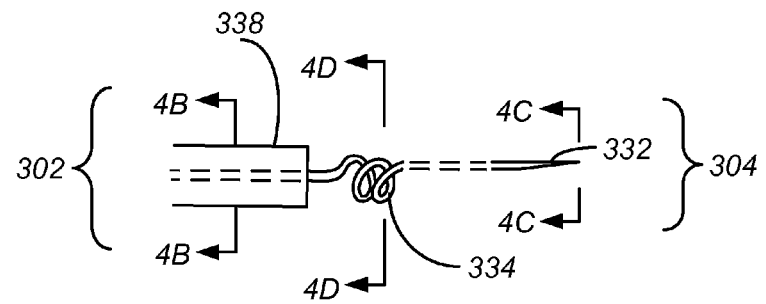
FIG. 4A
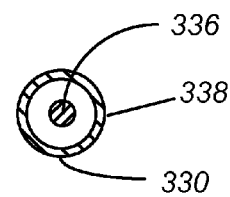
FIG. 4B
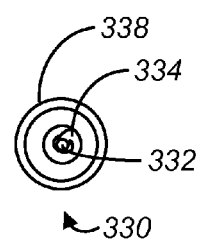 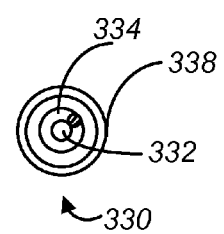
FIG. 4C　　　　FIG. 4D

TRANSCORONARY SINUS PACING SYSTEM, LV SUMMIT PACING, EARLY MITRAL CLOSURE PACING, AND METHODS THEREFOR

CROSS-REFERENCE

This application is a continuation application of U.S. patent application Ser. No. 11/770,371, filed Jun. 28, 2007 now U.S. Pat. No. 8,068,920, which claims the benefit of U.S. Provisional Application Ser. No. 60/828,708, filed Oct. 9, 2006 and U.S. Provisional Application Ser. No. 60/827,967, filed Oct. 3, 2006, which are incorporated herein by reference in their entirety.

BACKGROUND OF THE INVENTION

Ventricular pacing has been a useful technique for at least 50 years, and transvenous pacing for nearly that long. In the transvenous pacing system the lead is placed from a vein, usually in the thorax, and threaded into the right ventricle 22 of the heart 10. The lead in the right ventricle 22 permits pacing and sensing within that chamber. Of course, pacing from the right ventricle 22 depolarizes the heart in a completely different way than the heart is normally depolarized and does not make use of the patient's own, usually diseased, conduction system. The indication for pacing is an impairment of the patient's conduction system which prevents the system from being able to transmit electrical impulses that allow the heart to depolarize. The depolarization process is what leads to contraction in the cardiac muscle and a beat of the heart. Ventricular pacing, however, while very effective in preventing deaths from such entities as complete heart block, has several problems associated with it. One problem associated with ventricular pacing is pacemaker syndrome, which is a hemodynamic abnormality that can result when use of ventricular pacing is, for example, uncoupled from the atrial contraction. It can also result from a less effective contraction caused by the abnormal mechanism of depolarization caused by the right ventricular pacing catheter. In other words, the heart, depolarized from the right ventricular apex, does not squeeze as efficiently as the heart would have squeezed if it had been depolarized by its own conduction mechanism. Patients sense the decline in cardiac output when their pacemaker kicks in. In other patients, pacing induces a long term malfunction of the heart called cardiomyopathy that is caused by this slower depolarization of the heart and the associated decline in pump efficiency.

Over the past five to six years, first Medtronic and then other companies have developed devices to counter the deleterious effects of ordinary right ventricular apex pacing. The basic idea is to use two different pacing catheters in different parts of the ventricles 22, 26 to simultaneously depolarize the heart. This is called biventricular (or biV) pacing. Biventricular pacing (also referred to as cardiac resynchronization therapy (CRT)) uses leads that stimulate the right ventricle 22 from the apex and the left ventricle 26 from the lateral wall via the coronary sinus. One of the electrodes is the standard right ventricular apical pacing catheter and the other is a left ventricular lead usually placed, as indicated above, on the posterior left ventricular wall 15 through a vein branch 6 of the coronary sinus 5. When these two leads are hooked together to the same generator and simultaneously stimulate the ventricle, it takes less time to depolarize the ventricle and therefore a more synchronous contraction of the muscle ensues. The heart pumps blood more efficiently.

Biventricular pacing is also indicated for patients with congestive heart failure (CHF) due to left ventricular dysfunction. It is estimated that in approximately 30% of patients with heart failure, an abnormality in the heart's electrical conducting system causes the heart to beat in an asynchronous fashion. That is, the left ventricle fails to contract toward its theoretical center of mass. This asynchrony greatly reduces the efficiency of the heart in some patients with heart failure. Biventricular pacing resynchronizes the contraction of the heart by shortening the actuation time of the ventricles. Biventricular pacemakers differ from other pacemakers, which pace only the right ventricle 22. Biventricular pacing systems (BVPS), as they are currently constituted, require an operator to thread a catheter from an introducer in the coronary sinus 80 down into a vein branch 82 of the coronary sinus 80, shown in FIG. 1C, and then wedge that lead into the branch 82 to hold it in position. This technique has been useful but has had some difficulty associated with it and therefore a supplanting technique to solve such difficulty is desirable. Additionally, one of the risks associated with placement of the device is the potential to damage the coronary sinus or coronary veins by, e.g., dissection or perforation.

Biventricular pacing has now demonstrated utility in several situations. For example, it reverses the symptoms in patients with the pacemaker syndrome described above. It also improves many cardiomyopathies caused by long term pacing. In addition, it improves cardiac contraction in some patients who have enlarged ventricles 22, 26 and prolonged QRS duration who are suffering from heart failure. It has been sufficiently useful so that it is now included in many of the latest models of internal cardioverters and defibrillators (ICD) which are used to treat patients with heart failure and arrhythmia. See, for example, InSync Sentry™ and InSync Maximo™ (www.medtronic.com). Biventricular pacing is now a standard part of the armamentarium and medical science accepts that biventricular pacing, because it leads to more synchronous contraction, is a better way to pace patients than pacing from the right ventricular apex alone. A conventional implantable medical device, such as an ICD, is coupled to a patient's heart by leads such that the patient's heart forms part of the circuit. The device may include, for example, a pacemaker or defibrillator or any device that performs pacing or defibrillating functions. A housing houses a battery and pacing or defibrillating circuitry. Each lead typically is adapted to engage at least one stimulating electrode for delivery of electrical impulses to excitable myocardial tissue. The leads can be unipolar or bipolar.

Notwithstanding the clinical benefits of biventricular pacing, correctly placing the LV lead to achieve optimum performance may be difficult. The placement of the first lead, the one that goes in the right ventricle 22, has been standard for fifty years. When biventricular pacing was first tried, the placement of the second left ventricular lead was done surgically. However, the surgical procedure requires a small incision in the chest and most cardiologists cannot do this and do not want to refer patients to surgeons. Therefore, the standard cardiologic technique for LV lead placement now requires placement of a sheath from the subclavian vein into the coronary sinus 80 and through that sheath, an angiogram of the coronary sinus 80 can be obtained. From the angiogram the branches 82 of the coronary sinus 80 can be identified and a small pacing catheter is then directed through the coronary sinus and into the small coronary sinus vein 82 (see FIG. 1C) where it is lodged. The guiding catheter is then removed and the patient has a lead on the posterior left ventricular wall 15 (see FIG. 1C). The exact location of the lead is therefore a prisoner of the accidental anatomy of the veins that feed into the coronary sinus 5. The optimal location of the left ventricular lead and solutions for routine pacing from this location have not previously been discussed.

SUMMARY OF THE INVENTION

Biventricular pacing systems (BVPS), as they are currently constituted require an operator to thread a catheter from an introducer sheath in the coronary sinus down into a vein branch of the coronary sinus, shown in FIG. 1C, and then wedge a lead into the vein branch to hold the lead in position. This technique has been useful but has had some difficulty associated with it and therefore a technique for LV (Left Ventricular) summit pacing to supplant this technique is desirable.

An aspect of the invention is directed to a series of ideas, tools and techniques that will permit an operator to place a pacing catheter or electrode lead from a sheath within the coronary sinus through the coronary sinus wall and embed that pacing catheter in the posterior left ventricular summit. Such a pacing catheter can then be the critical second lead in a biventricular pacing system.

The posterior summit of the left ventricle has been identified as the ideal location for an LV pacing lead because it optimizes early closure of the mitral valve in addition to reducing the time that it takes to activate the ventricle with BiV pacing. A permanent pacing electrode introduced by Seldinger technique that pierces the coronary sinus and achieves a stable location on the summit of the left ventricle is disclosed. A double lumen sheath that can place the pacing catheter in the coronary sinus and facilitate lodging it in the summit of the posterior LV is disclosed. A method for correlating angiographic coronary anatomy with live fluoroscopic pacing catheter placement is provided. Finally, a method for using intravascular ultrasound with pacing catheter placement is provided. These methods should help prevent damage to any coronary artery and prevent perforation of the epicardium (not shown) when the left ventricular summit (LV summit) is pierced.

An aspect of the invention is directed to a guiding catheter comprising an elongate sheath having a distal end, a proximal end, a first lumen and a second lumen wherein the first lumen has a first lumen exit port distal to a second lumen exit port and the distal end is configured to lodge within a coronary sinus of a heart distal to a summit of a left ventricle.

Another aspect of the invention is directed to a transcoronary sinus pacing system. The system comprises: an elongate sheath, or guiding catheter, having a distal end, a proximal end and two lumen therethrough; a pacing catheter the tip of which is adapted to perforate the coronary sinus and lodge in the LV summit, wherein the catheter can be advanced within the lumen of the elongate sheath and placed in the summit of the left ventricle without identification of coronary vein anatomy.

In some configurations, the elongate sheath can be steerable by a guidewire. Additionally, the elongate sheath further provides radiopaque markers to facilitate locating the distal end of the device in situ. The elongate sheath can also have a teardrop cross-section which is used to determine orientation of the exit port relative to target anatomy. Furthermore, the pacing catheter is positioned anatomically in order to optimize early closure of the mitral valve. Positioning of the pacing catheter can reduce the time required to activate the left ventricle. As a result of these configurations, the pacing catheter is positioned in the heart irrespective of the anatomical position of the veins of the coronary sinus, while still optimizing performance. The pacing catheter can furthermore have a tip configured to pierce the coronary sinus.

Additionally, one or more imaging systems can be provided that assist in placement of the pacing catheter in the summit of the left ventricle while avoiding piercing coronary arteries. Suitable imaging systems would be known to those skilled in the art and include, for example, recorded angiographic image systems, live fluoroscopy systems, and live intravascular ultrasound.

Another aspect of the invention is directed to a left ventricular summit pacing device. The left ventricular summit pacing device comprises: an elongate sheath having a distal end, a proximal end and two lumen; and a pacing catheter the tip of which can perforate the coronary sinus and lodge in the LV summit. The elongate sheath is steerable by a guidewire, can provide radiopaque markers and/or have a teardrop cross-section. Additionally, the pacing catheter can be anatomically positioned in order to optimize early closure of the mitral valve. In some aspects, the pacing catheter is configured to reduce the time required to activate the left ventricle. The pacing catheter can be placed irrespective of the anatomical position of the veins of the coronary sinus and can have a tip configured to pierce the coronary sinus.

Still another aspect of the invention is directed to an early mitral valve closure pacing device. The early mitral valve closure pacing device comprises: an elongate sheath having a distal end, a proximal end and two lumen; and a pacing catheter having a pacing needle the tip of which can perforate the coronary sinus and lodge in the LV summit. The elongate sheath is steerable by a guidewire and provides one or more radiopaque markers to identify its orientation in the coronary sinus. The elongate sheath can also be configured to have a teardrop cross-section. The provision of radiopaque markers and cross-sectional shaping facilitates identification of the position and orientation of the device in situ. The pacing catheter can further be anatomically positioned in order to optimize early closure of the mitral valve and to reduce the time required to activate the left ventricle. The pacing catheter is configured for placement irrespective of the anatomical position of the veins of the coronary sinus. Additionally, the pacing catheter can be configured to provide a tip configured to pierce the coronary sinus.

An aspect of the invention is directed to a method for implanting a pacing device through the coronary sinus into the summit of the left ventricle. The method comprises the steps of: introducing a sheath; steering the sheath to a target location within the coronary sinus; lodging a distal end of the sheath beyond a posterior summit of the left ventricle; advancing a pacing lead through a lumen of the sheath to the target location within the coronary sinus; perforating the coronary sinus with the pacing lead; and removing the sheath. Additionally, the method can include the steps of advancing a right ventricular pacing catheter to a target location within the heart; and positioning an electrode at the target location within the heart. In some instance, an additional step of correlating an angiogram with live fluoroscopy is performed; or correlating an angiogram with live intravascular ultrasound. The pacing device is implanted through the coronary sinus into the summit of the left ventricle. Once implanted, the summit of the left ventricle can be activated to initiate closure of the mitral valve early in systole. Additionally, the cross-sectional shape of the device can be used in the method to facilitate steering and perforating.

Another aspect of the invention is directed to a method for achieving early closure of a mitral valve. The method comprises the steps of: introducing a sheath; steering the sheath to a target location within the coronary sinus; advancing a pacing lead via a catheter through a lumen of the sheath to the target location within the coronary sinus; and perforating the coronary sinus with the pacing lead. Additionally, a right ventricular pacing catheter can be advanced to a first target location within the heart. Thereafter a first electrode can be positioned at the first target location within the heart. Images can be taken and the images, such as an angiogram and a live fluoroscopy, can be correlated. Alternatively, an angiogram can be correlated with live intravascular ultrasound. The target location within the coronary sinus is a left ventricular pacing summit. Additionally, the method can comprise the step of activating the LV summit to achieve early closure of a mitral valve during systole. Furthermore, the cross-sectional shape of the device can be used to facilitate the steering the device and perforating the summit.

INCORPORATION BY REFERENCE

All publications, patents and patent applications mentioned in this specification are herein incorporated by reference to the same extent as if each individual publication, patent or patent application was specifically and individually indicated to be incorporated by reference.

BRIEF DESCRIPTION OF THE DRAWINGS

FIG. 4A illustrates a pacing needle electrode and pacing catheter;

FIG. 4B illustrates a cross-sectional view of a pacing lead within a pacing catheter viewed along line 4B of FIG. 4A;

FIG. 4C illustrates a axial view of a pacing needle within a pacing catheter viewing the device proximally from line 4C of FIG. 4A;

FIG. 4D illustrates an axial cross-sectional view of a pacing needle within a pacing catheter viewing the device proximally beginning at line 4D of FIG. 4A;

DETAILED DESCRIPTION OF THE INVENTION

Figure 1A:
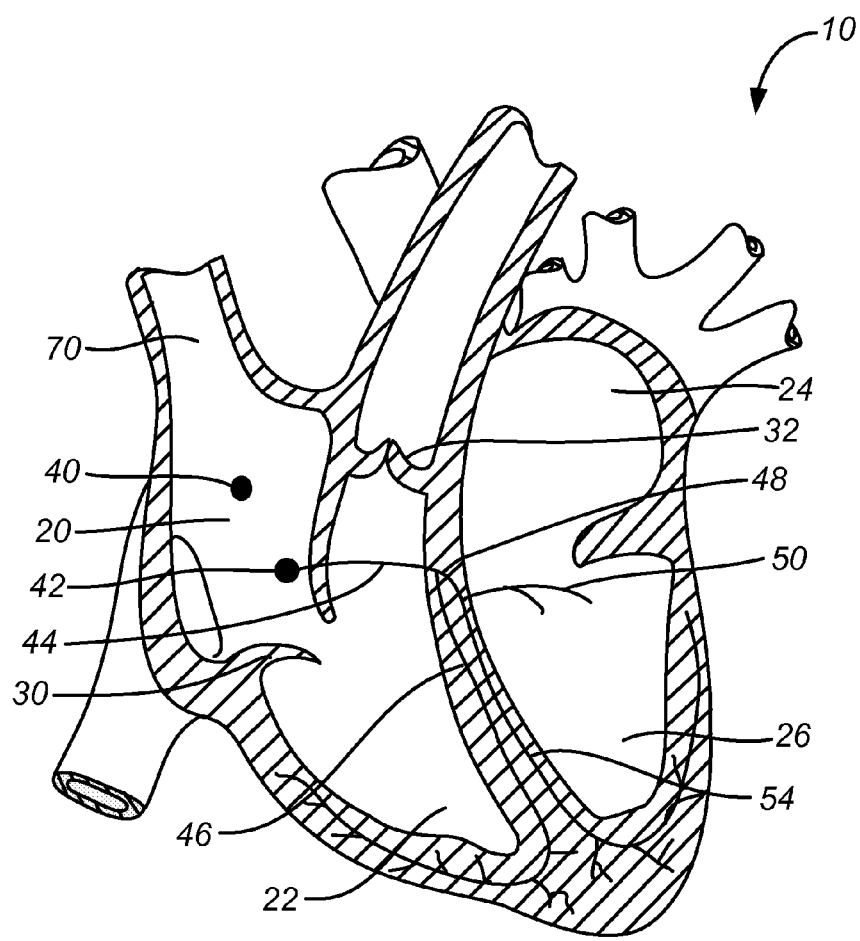
FIG. 1A illustrates a cross-sectional view of the normal ventricular conduction mechanism.

This system obviates the need for a separate lead placed in a coronary sinus vein 82 for transcoronary sinus pacing systems, as is currently practiced. The system relies on a the use of a single pacing catheter, which acts as an electrode lead, that is advanced through a guiding catheter to be positioned directly in, or near, the summit 28 of the left ventricle 26. Once positioned, the pacing catheter perforates the wall of the coronary sinus 66, locates the summit 28 of the left ventricle 26 a few millimeters from the place where the perforation occurs, and engages the summit 28 of the left ventricle 26 with an electrode tip. The actual location of perforation will be governed by patient specific anatomy and may vary slightly to avoid perforation of a coronary artery or ending up in the pericardium.

In order to appreciate the novelty of the invention, it is important to understand the basics of the human conduction system of the heart 10. The normal human conduction system carries an impulse from the atria to the ventricles 22, 26 and distributes the electrical impulse very efficiently so that the entire ventricle is electrically activated in less than 100 milliseconds. This permits effective ventricular contraction. In contrast, RV apex pacing activates the heart 10 in 150-200 or more milliseconds. This longer time leads to a less synchronous ventricular contraction and often to lower cardiac output and the other complications described above.

FIG. 1A depicts the normal ventricular conduction mechanism of a heart 10. The normal ventricular conduction mechanism starts with a bridge from the atrium to the ventricles called the atrioventricular node (AV node) 42. The AV node 42 is activated by the sinu-atrial node (SA node) 40. Once an impulse passes through the AV node 42, the impulse then passes through the bundle of His 44, which is at the base of the ventricles 22, 26. Thereafter, the conduction system divides into a left main branch 48 and right main branch 46. The left branch 48, which activates the left ventricle 26, almost immediately divides into a small anterior branch 50 and a much larger posterior branch of the left main branch 54 that swings around the left ventricle 26 and basically surrounds the posterior mitral annulus (not shown) before it spreads out over the ventricles 22, 26. This important left posterior branch 54 has not been well understood until recently. The posterior branch 54 activates the left ventricle summit early in systole and starts the process by which the mitral valve 34 closes.

As it turns out, the heart 10 as a pump cannot generate much force until the mitral valve 34 is closed and isovolumic systole can begin. At that point, the heart 10 can generate force because the blood inside it is trapped until the pressure inside that chamber exceeds that of aortic pressure at which point the blood is ejected from the ventricle into the aorta.

Figure 1B:
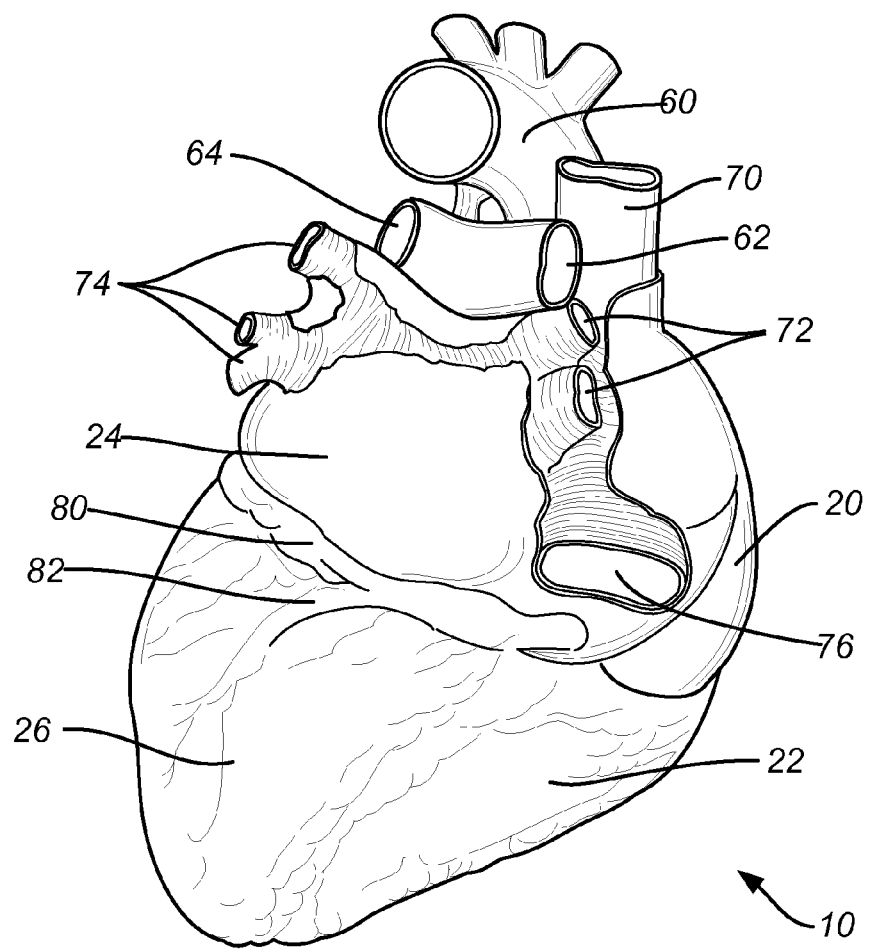
FIG. 1B illustrates a posteroinferior view of the heart.

FIG. 1B depicts a posteroinferior view of the heart 10, showing the relative positions of the aortic arch 60, the left pulmonary artery 64, the right pulmonary artery 62, the left pulmonary veins 74, the right pulmonary veins 72, the left atrium 24, the coronary sinus 80, a branch of the coronary sinus 82, the left ventricle 26, the right atrium 20, the right ventricle 22, the superior vena cava 70, and the inferior vena cava 76. If the summit 28 of the left ventricle 26 is not activated early, the mitral valve 34 leaks and the heart cannot generate as much force. A lower cardiac output ensues. Therefore, the optimal position for a left ventricular pacing device, such as the pacing catheter 110, is in the mid-position on the posterior summit 28 of the left ventricle 26 (the LV summit) In FIG. 1C an example optimal location for actual left ventricular pacing is marked (with an "X"). As will be appreciated by those skilled in the art, the actual optimal location for pacing will vary slightly from patient-to-patient as a function of the individual's coronary anatomy.

Figure 1C:
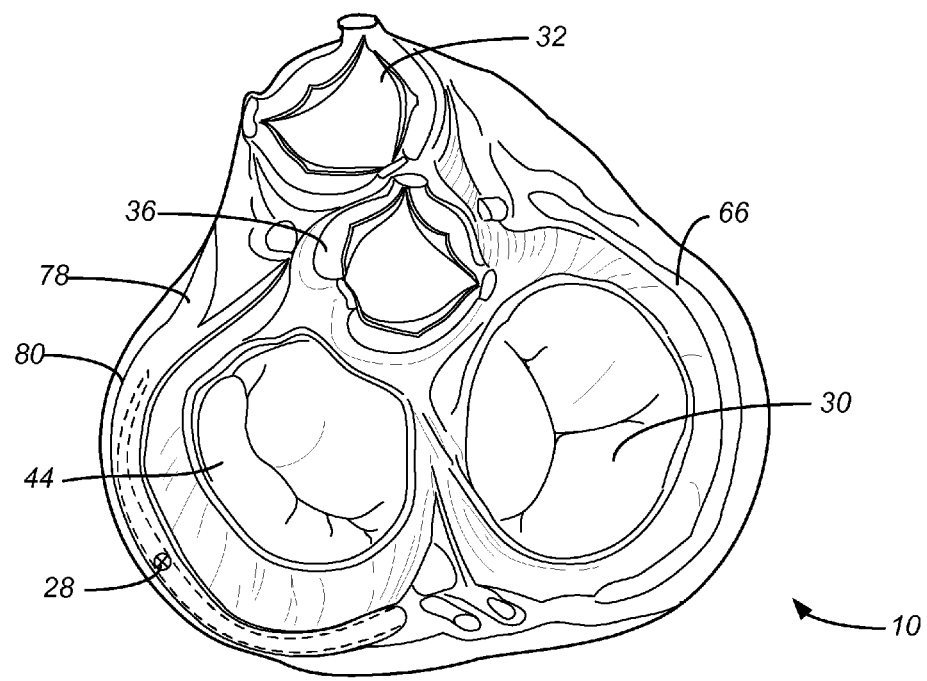
FIG. 1C illustrates a cross-sectional view of heart in systole showing approximate summit of left ventricle.

FIG. 1C depicts a cross-sectional view of heart 10 in systole showing the approximate summit 28 of the left ventricle 26. FIG. 1C also shows the relative positions of the aortic valve 36, the pulmonary valve 32, the right coronary artery 66, the mitral valve 34, the tricuspid valve 30, the coronary sinus 80, and the great coronary vein 78, a branch 82 of the coronary sinus 78. The circumflex artery (not shown) is generally coincident with or generally near the coronary sinus 78 depicted in FIG. 1C around the mitral valve 34.

Figure 1D:
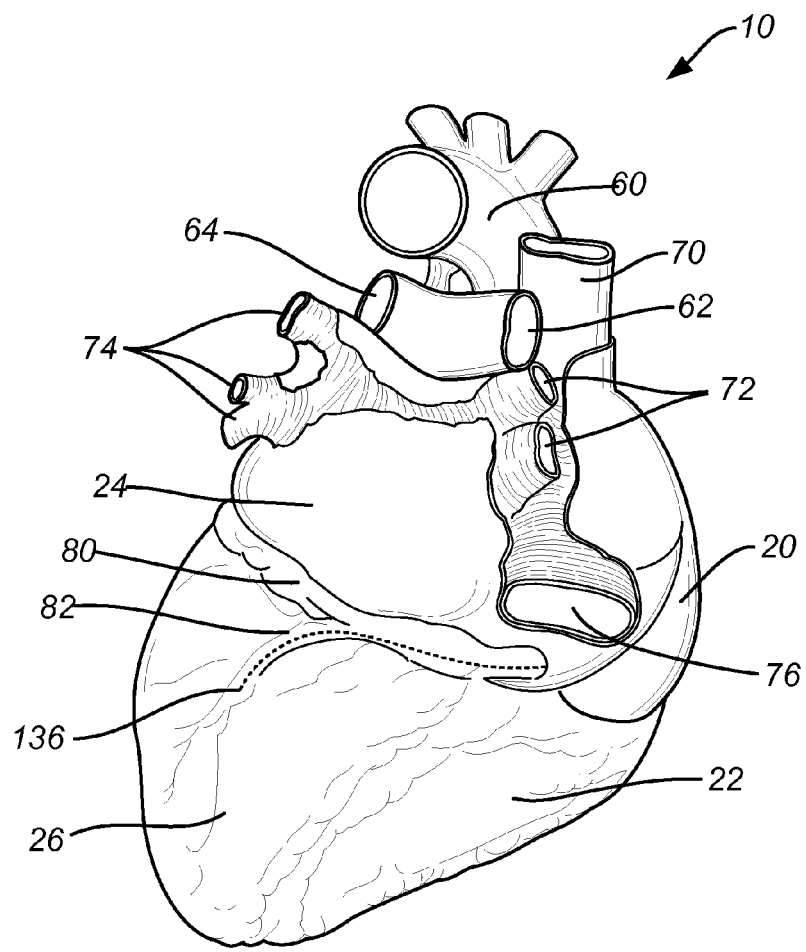
FIG. 1D illustrates a posteroinferior view of the heart showing LV pacing lead placement in a coronary sinus vein.

Currently available systems deviate from this optimal location because of the variability of branch veins 82 of the coronary sinus 78. Although the mid-portion near the summit 28 is the optimal location, the veins 82 of the coronary sinus 78 can occur anywhere posteriorly and therefore cardiologists are forced to put them wherever they find a vein 82. FIG. 1D depicts a posteroinferior view of the heart showing a LV pacing lead 136 placed in a coronary sinus branch vein 82. FIG. 1D also shows such lead placement and its relative position to aortic arch 60, the left pulmonary artery 64, the right pulmonary artery 62, the left pulmonary veins 74, the right pulmonary veins 72, the left atrium 24, the coronary sinus 80 generally, the left ventricle 26, the right ventricle 22, the superior vena cava 70, and the inferior vena cava 76.

In addition, some patients do not have proper sized veins and so the anatomy of some patients does not permit the current placement of a transvenous left ventricular lead. The importance of the exact location of the pacing device on the summit 28 of the left ventricle 26 has, heretofore, not been fully appreciated. Currently the focus has been on another important idea: having the two pacing leads, the one in the right ventricle 22 and the one in the left posterior ventricle 26, as far apart as possible in order to reduce the time that it takes to activate the entire left ventricular mass. However, it is additionally important, but unappreciated, that the LV summit 28 pacing occurs such that it closes the mitral valve 34 early in systole and thereby permits isovolumic systole to occur.

Thus, it is appreciated herein that the LV summit 28 of the posterior left ventricular wall, the mid-portion 28 of the posterior left ventricle 26 (e.g., the left ventricle summit, or posterior LV summit) is the ideal location for a second pacing wire because it starts the process of closing the mitral valve 34 and therefore facilitates isovolumic systole. Additionally, this location is as far as it can be from the RV apex with respect to physical location in the heart, thus pacing electrode placement in the mid-portion 28 of the posterior left ventricle 26 also reduces the amount of time it takes for electrical activity to depolarize the heart. Cardiologists to date have not focused on this idea of early closure of the mitral valve 34 because they had no reliable way to pace in this area. They have been forced to lodge a pacing catheter in whatever vein 3 they find in the posterior left ventricle regardless of its exact location relative to the summit 28 of the left ventricle 26.

Additionally, pacing the posterior LV summit 28 by perforating the coronary sinus 80 with a sharp electrode is also considered part of the invention. The sharp electrode perforates the LV summit 28 wall which is just a few millimeters below the coronary sinus 80 and in that location it will be near the ideal spot for LV pacing.

I. Devices

Figure 2A:
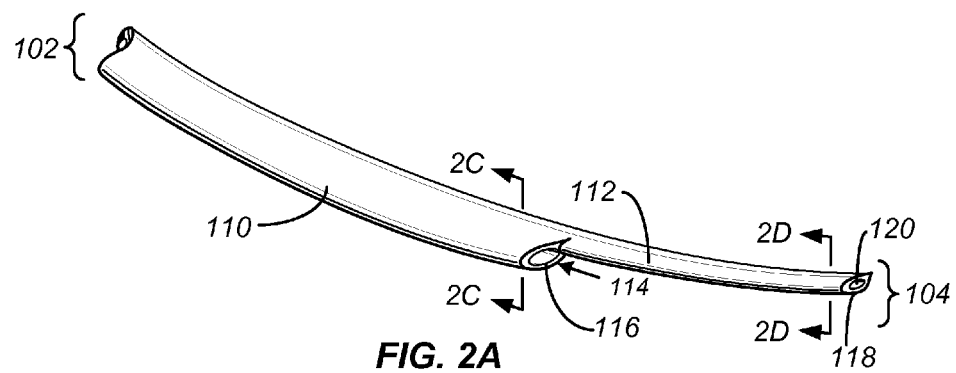
FIG. 2A illustrates an external view of the distal end of a guiding catheter.
Figure 5:
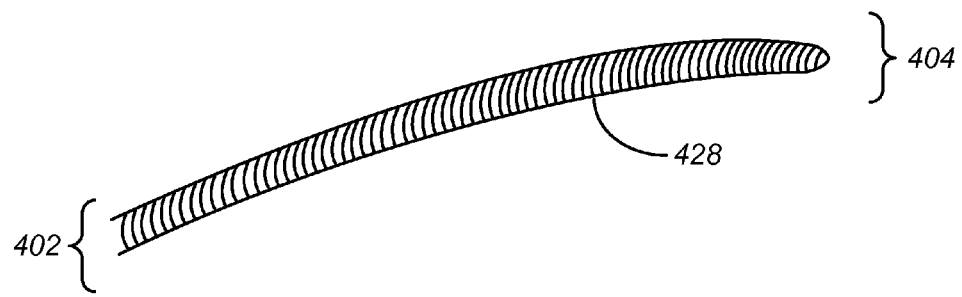
FIG. 5 illustrates a distal end of a guidewire.

FIG. 2A depicts an external view of a distal end of a guiding catheter 110. The guiding catheter 110 is typically a long fine catheter specially designed for passage, usually through a subclavian vein, into the heart under roentgenologic control to provide therapeutic intervention. The guiding catheter 110 can be in the form of a tear-drop cross-sectioned sheath having two lumens 116, 120 each of which has a distal exit port, spaced apart from each other, along the length of the catheter. The first guidewire lumen 120 provides a guidewire exit port 118 at or near, the distal end 102 of the catheter from the catheter nose 112. The guidewire entrance port (not shown) is positioned proximally relative to the exit port. As will be appreciated by those skilled in the art, the position of the entrance port can vary according to a particular design and desired functionality. Additionally, the guidewire lumen 120 is configured to enable a guidewire (not shown) to easily pass through its lumen 120 during use. The guidewire facilitates guiding the entire guiding catheter 110 system through the patient's blood vessels to a target region, such as the coronary sinus 80. A distal end 404 of the guidewire 440 is shown in FIG. 5. The guidewire may be of a type that is more flexible at its distal end 404 than at its proximal end 402. Additionally, the distal end of the guiding catheter 110 has a nose 112, having a smaller radius than a proximal radius of the guiding catheter 110, that is configured to wedge into the coronary sinus to facilitate positioning the pacing catheter exit port 114 optimally relative to the posterior LV summit. To achieve this, the dimensions of the distal end of the device (where only one lumen is present) is smaller than a proximal end of the device (where two lumens are present), as appreciated from the cross-sections shown in FIGS. 2C-D.

Figure 7A:
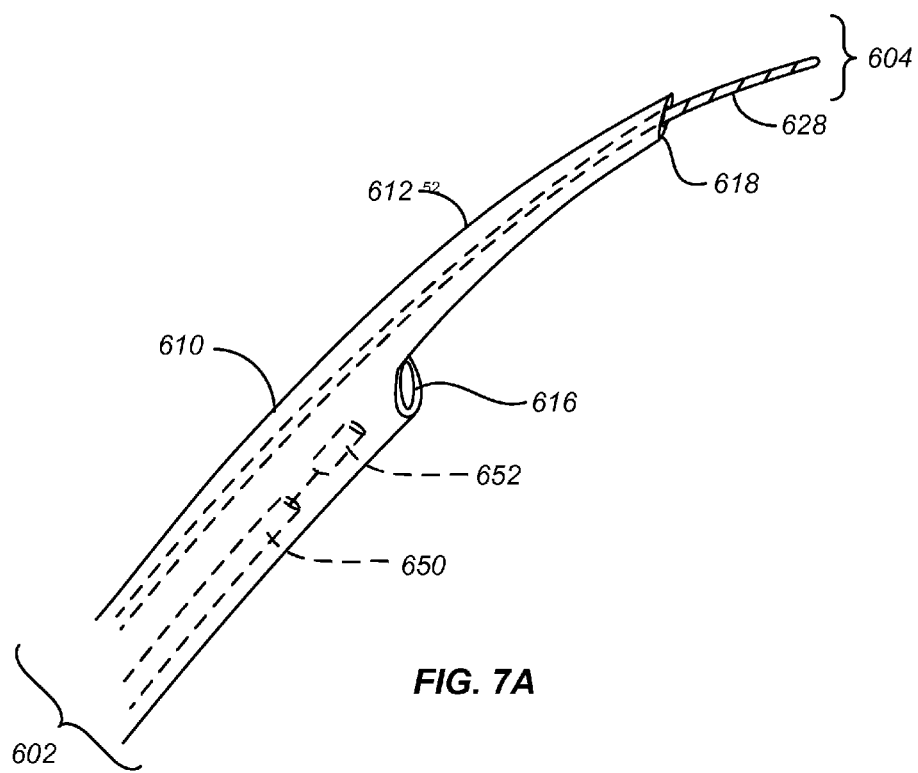
FIG. 7A illustrates an ultrasound assembly system comprising a guiding catheter advanced along guidewire, and an ultrasound catheter within the guiding catheter lumen.
Figure 7B:
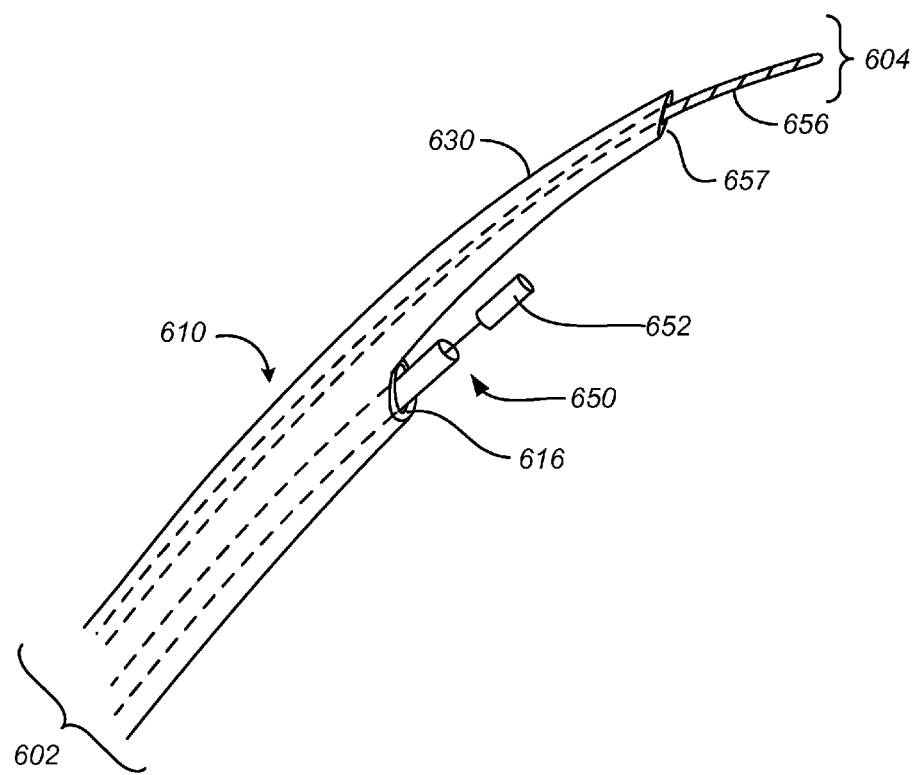
FIG. 7B illustrates a guiding catheter advanced along a guidewire, and showing an ultrasound catheter advanced through the guiding catheter lumen.

The second pacing catheter lumen 116 of the guiding catheter 110, which may be a larger lumen to accommodate various working devices, may be configured to carry the pacing catheter 230, such as that shown in FIG. 3, and is discussed further below. The pacing catheter lumen 116 has a pacing catheter exit port 114 that is positioned along the length of the guiding catheter such that the pacing catheter exit port 114 is positioned near the distal end 104 of the guiding catheter 110 but is proximal relative to the guidewire exit port 118. The pacing catheter lumen 116 may further carry other therapeutic and diagnostic devices, such as an ultrasound catheter 650, as shown in FIGS. 7A and 7B, and discussed further below. The pacing catheter lumen 116 may also carry fluoroscopic material to flush the coronary anatomy in order to facilitate vasculature visualization during fluoroscopy and angiography, including visualization of radiopaque markers. Further, the pacing catheter lumen 116 may also carry fluoroscopic material simultaneously with the pacing catheter, such as pacing catheter 230 shown in FIG. 3, or another therapeutic or diagnostic device, such as an ultrasound catheter 650 shown in FIG. 7. The markers assist in allowing the physician to determine which was the catheter is advanced during the procedure.

Figure 2B:
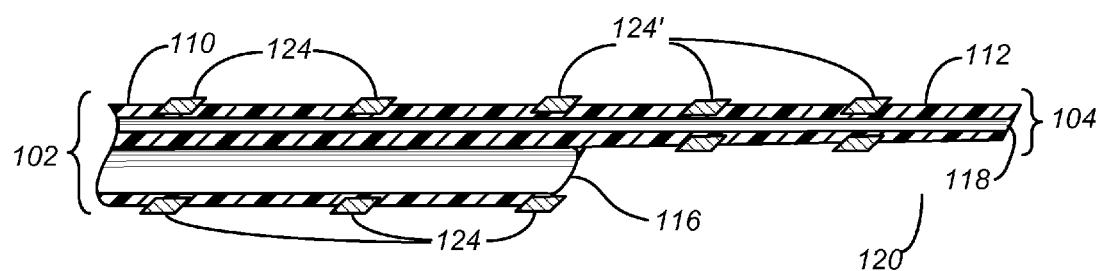
FIG. 2B illustrates a cross-sectional view of the distal end of a guiding catheter along the longitudinal axis and showing radiopaque markers.

FIG. 2B depicts a cross-sectional view of the distal end 104 of a guiding catheter 110 along its longitudinal axis showing radiopaque markers 124, 124'. More or fewer markers may be used to optimally visualize the location of the guiding catheter 110 within the coronary sinus 80. The radiopaque markers 124 can be positioned in order to visualize the location of the pacing catheter exit port 114 (distally within the coronary sinus 80) as well as its orientation within a patient's vasculature. The radiopaque markers 124 depicted in FIG. 2B can provide fine adjustment before inserting the pacing catheter (shown below). The radiopaque markers 124 allow an operator to orient the guiding catheter 110 and the pacing catheter exit port 114 fluoroscopically with respect to the actual shape of the patient's left ventricle 26. Thus, when the pacing catheter (shown below) is advanced through the guiding catheter 110 and extends distally out of the pacing catheter exit port 114 it will be positioned to pierce the coronary sinus 80 at the summit 28 of the left ventricle 26 and will not, for example, end up outside the heart 10. The use of such visualization aids the operator in the proper placement of the pacing electrode needle (shown below) and anchor (shown below) at the LV summit 28 while avoiding perforating a coronary artery or ending up in the pericardium (not shown).

As will be further appreciated, a variety of configurations for the guidewire lumen can be employed without departing from the scope of the invention. For example, the guidewire lumen can be configured to provide a distal exit port 118 at the guiding catheter distal tip 112 or catheter nose as shown in FIG. 2B, and a proximal exit port (not shown) which extends through the guiding catheter 110 only to about the same location along the length of the catheter as the pacing catheter exit port 114. In an alternative configuration, the guidewire lumen and proximal exit port of the guiding catheter 110 may extend farther proximally, or extend the entire length of the catheter as an over-the-wire embodiment. The guiding catheter may also be configured to be stiffer proximally for increased catheter pushability and steerability during use.

Also as illustrated in FIG. 2A and FIG. 2B the guiding catheter 110 has a long, flexible nose 112 and a body 122. This nose 112 provides a stable platform for advancing the pacing catheter (shown below) and for permitting the operator to bend the sheath 122 at the site of the larger pacing catheter lumen 116. The nose 112 permits the operator to bias the pacing catheter exit port 114 toward the LV summit 28 before advancing the pacing catheter (shown below) is advanced distally out of the pacing catheter exit port 114.

Figure 2C:
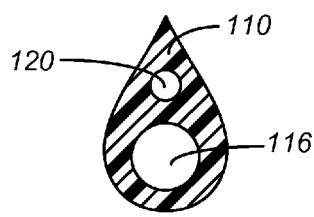
FIG. 2C illustrates an axial view of the distal end of the guiding catheter of the embodiment depicted in FIG. 2A along line 2C of FIG. 2A.

FIG. 2C depicts an axial view from the distal end of the guiding catheter 110 of the guiding catheter shown in FIG. 2A facing proximally along line 2C of FIG. 2A. Also depicted is the pacing catheter lumen 116. As depicted, the cross-sectional shape of the device is teardrop shaped in order to aid operator manipulation the device from the proximal end to visualize, steer, manipulate, and position the guiding catheter 110 at its distal end 104 within the coronary sinus 80. The teardrop shape, also depicted in FIG. 2D, additionally helps the user orient the guiding catheter 110 correctly within the coronary sinus 80. As will be appreciated by those skilled in the art, the use of a teardrop shape profile also enables a user to determine at a proximal end the orientation of the distal end of the device, thereby facilitating steering and positioning.

Figure 2D:
FIG. 2D illustrates an axial view of the distal end of guiding catheter nose along line 2D of FIG. 2A.

FIG. 2D depicts an axial view of distal end of the guiding catheter nose 112 of the embodiment depicted in FIG. 2A facing proximally along line 2D of FIG. 2A. The long nose 112 of the guiding catheter 110 beyond the location of the larger pacing catheter lumen 116 (shown above) is thin and flexible and is designed to lodge the guiding catheter 110 securely in the coronary sinus so that the pacing catheter exiting from the pacing catheter lumen can be securely advanced through the coronary sinus without movement of the guiding catheter 110.

Figure 3:
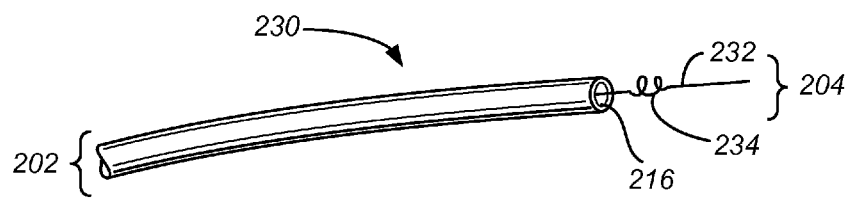
FIG. 3 illustrates an external view of a pacing needle electrode and a pacing catheter.

FIG. 3 depicts an external view of an embodiment of a pacing catheter 230 and a pacing needle electrode 232. This view also shows a pacing needle anchor 234 (pigtail) of an embodiment. The pacing catheter is composed of the needle that perforates the coronary sinus and enters the LV summit, the screw in device just behind it that anchors the needle within the LV summit, and a pacing wire that extends back to the location of the pacing device usually placed subcutaneously under the clavicle. Once positioned and attached to a control device, such as the ICD, the position of the electrode reduces the amount of time required to activate the left ventricle.

FIG. 4A also shows pacing catheter 330 needle electrode 332. In this view, the pacing catheter 330 is proximal to the pacing needle anchor 334. The pacing catheter 330 is shown at the distal tip of the device, and the embodiment is shown having an insulated portion 338 beginning at a point proximal to the exposed electrode 332. Insulation of the lead continues proximally from such point to ensure other areas of the heart are not exposed to an electrical signal when the lead 336 is activated. The pacing catheter 330 itself looks like a standard right ventricular screw-in electrode catheter but instead of having merely a simple corkscrew end there is a long needle 332 at the distal tip 304 of the pacing catheter 330 which is approximately 1 centimeter long and which extends distally beyond the screw-in anchor portion 334 of the device 330.

FIG. 4B shows cross-sectional view of the embodiment depicted in FIG. 4A comprising a pacing lead 336 within a pacing catheter 330 along line 4B of FIG. 4A. FIG. 4C depicts an axial view of the embodiment depicted in FIG. 4A comprising a pacing needle 332 within the insulated portion 338 of the pacing catheter 330 viewing the embodiment proximally from line 4C of FIG. 4A. FIG. 4D depicts an axial cross-sectional view of the embodiment depicted in FIG. 4A comprising a pacing needle electrode 332 within a pacing catheter 330 viewing the embodiment proximally beginning at line 4D of FIG. 4A.

FIG. 5 illustrates a guidewire 428. Suitable guidewire designs would be known to a person skilled in the art and include, for example, those described in U.S. Pat. No. 7,089, 065 for Modified guidewire for left ventricular access lead;

U.S. Pat. No. 6,973,352 for Steerable cardiac pacing and sensing catheter and guidewire for implanting leads; U.S. Pat. No. 6,671,560 for Modified guidewire for left ventricular access lead; U.S. Pat. No. 6,493,591 for Implantable active fixation lead with guidewire tip; U.S. Pat. No. 6,356,791 for Modified guidewire for left ventricular access lead; U.S. Pat. No. 5,549,109 for Sheathed multipolar catheter and multipolar guidewire for sensing cardiac electrical activity; U.S. Pat. No. 5,477,864 for Cardiovascular guidewire of enhanced biocompatibility; U.S. Pat. No. 4,917,102 for Guidewire assembly with steerable adjustable tip.

Figure 6A:
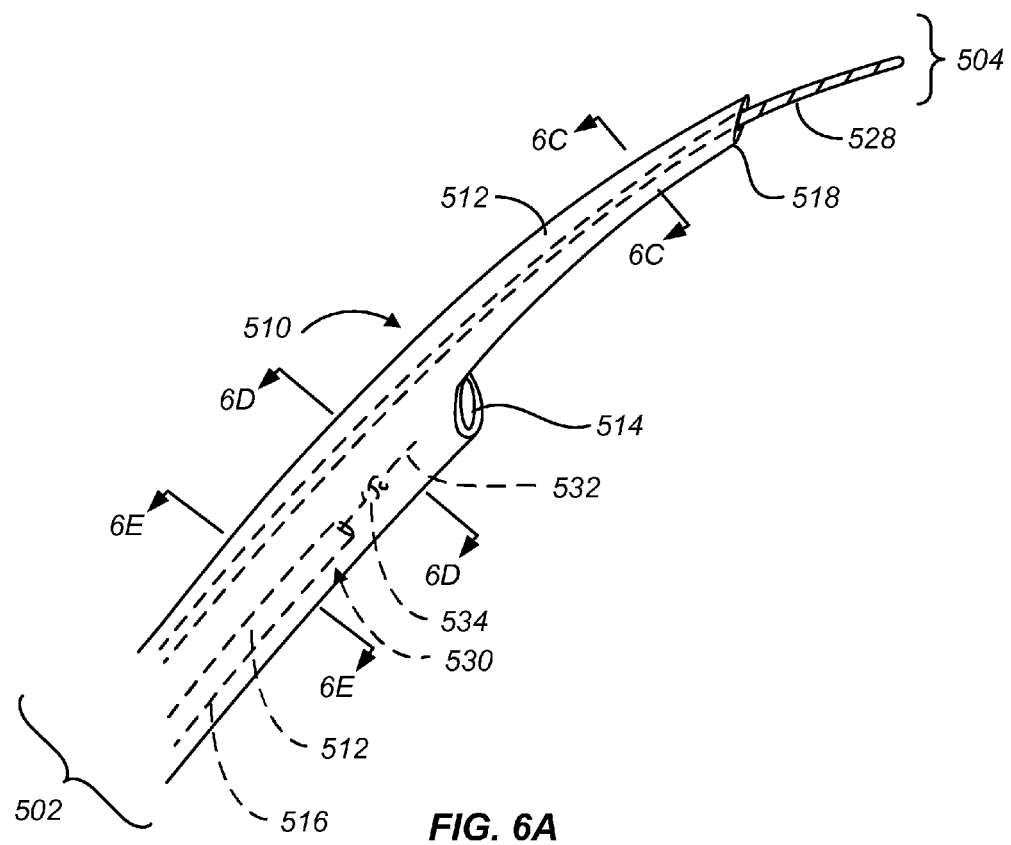
FIG. 6A illustrates a guidewire and a pacing catheter within an elongate sheath of the guiding catheter, with the pacing catheter still within the sheath.
Figure 6B:
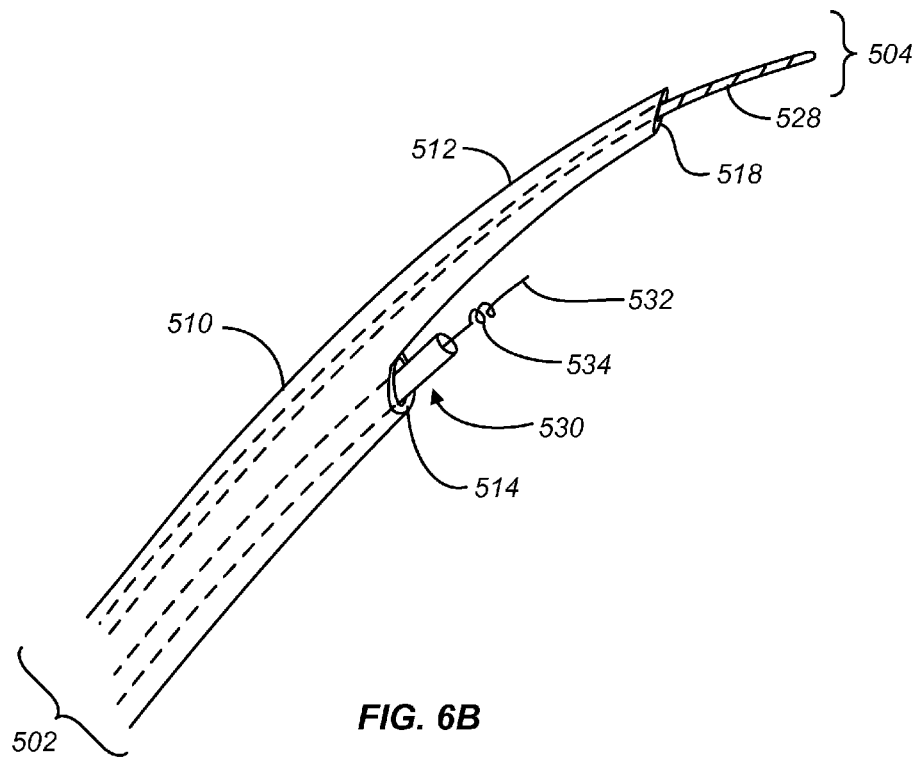
FIG. 6B illustrates a guidewire and a pacing catheter within an elongate sheath of the guiding catheter, with the pacing catheter advanced out the distal end of the sheath.

FIG. 6A shows an embodiment wherein a guidewire 528, an example of which is shown in FIG. 5, and pacing catheter 530 are positioned within lumens of the elongate sheath of the guiding catheter 510. The guiding catheter 510 is shown advanced along the guidewire 528 and the pacing catheter 530, having a pacing needle electrode 532 and a pacing catheter anchor 234, has been advanced within the pacing catheter lumen 516. The pacing catheter 530 is depicted within the pacing catheter lumen 516 of the guiding catheter 510 prior to exiting the pacing catheter exit port 514. In the embodiment depicted in FIG. 6B, the guiding catheter 510 has been advanced along the guidewire 528 and the pacing catheter 530, having a pacing needle electrode 532 and a pacing catheter anchor 534, has been advanced out the distal end of the elongate sheath of the guiding catheter 510. The guiding catheter 510 embodiments of FIG. 6A and FIG. 6B comprise a pacing catheter lumen 516, a pacing catheter exit port 514, a guiding catheter nose 512, a guidewire lumen 520, and a guidewire distal exit port 518.

Figure 6C:
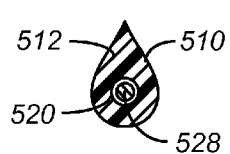
FIG. 6C illustrates a cross-sectional view of a guidewire within the nose of a guiding catheter along line 6C of FIG. 6A.
Figure 6D:
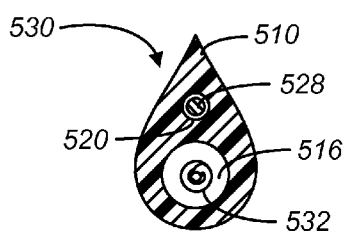
FIG. 6D illustrates an axial cross-sectional view of a pacing needle and a guidewire within the guiding catheter viewing the device proximally from line 6D of FIG. 6A.
Figure 6E:
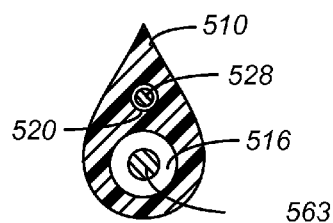
FIG. 6E illustrates a cross-sectional view of a pacing catheter, a lead and a guidewire within a guiding catheter along line 6E of FIG. 6A.

FIG. 6C, FIG. 6D, and FIG. 6C depict cross-sectional views of the embodiment depicted in FIG. 6A advanced along a guidewire 528 and having a pacing catheter 530 therein. FIG. 6C depicts a guidewire 528 within the guidewire lumen 520 of the elongate sheath or guiding catheter 510. In this view, only the nose 512 of the guiding catheter 510 is shown as a cross-section along line 6C of FIG. 6A. FIG. 6D depicts an axial cross-sectional view of the guiding catheter 510 of FIG. 6A which has been advanced along a guidewire 528 and has a pacing catheter 530 therein. In the FIG. 6D view, FIG. 6A is cut along line 6D, and the view is an axial cross-section looking proximally from line 6D of FIG. 6A. This view, thus, shows the pacing needle electrode 532 of the pacing catheter 530 within the pacing catheter lumen 520 of the guiding catheter 510, as well as the guidewire 528 within the guidewire lumen 520 of the guiding catheter 510. FIG. 6E depicts a cross-sectional view of pacing catheter 530, lead 536 and guidewire 528 within guiding catheter 510 cut along line 6E of FIG. 6A. In all views of the FIG. 6 embodiments, the guiding catheter 510 has a teardrop shape along its distal length at least, including along its nose 512. The teardrop shape of the guiding catheter 510 may extend the entire length of the catheter 510, or may stop at a first point proximal to the teardrop distal portion, and restart at a second point proximal to the first point.

Another way to address avoiding perforating a coronary artery lying on the LV summit 28 when piercing the coronary sinus 80 to anchor 234 the LV pacing electrode 532, is through visualization of the individual patient's coronary anatomy. Recording and storing appropriate coronary angiographic views and superimposing them on the live fluoroscopic views will prevent the operator from advancing the pacing catheter 530 into a location where a coronary artery branch (not shown) resides. Such a method can also assist in placement of the electrode 532 at the LV summit 28.

Additionally, as will be appreciated by those skilled in the art, other techniques can be used to determine the location of coronary arteries and to find and place an electrode 532 in the LV summit 28. For example, in addition to performing an angiogram, a physician can employ an intravascular ultrasound device 550 to determine the location of arteries. Use of any of the features described above alone or in combination with each other can reduce the likelihood of piercing a coronary artery or the pericardium and missing the LV summit 28.

Use of such a device in combination with an embodiment of the guiding catheter 610 described herein is depicted in FIG. 7A and FIG. 7B. FIG. 7A depicts an imaging system, such as an ultrasound assembly system, within a guiding catheter 610 described herein. Use of an imaging system can facilitate recording angiographic images and live fluoroscopy, or recorded angiographic images and life intravascular ultrasound. In this embodiment, a guiding catheter 610 having two lumens 616, 620 has been advanced along a guidewire 628 and an ultrasound catheter 654 has been advanced within the guiding catheter 610 second lumen 616 (pacing catheter lumen 616). The ultrasound assembly system, or the ultrasound catheter 654 and ultrasound device 650, is depicted within the pacing catheter lumen 616 of the guiding catheter 610 prior to exiting the pacing catheter exit port 614. In the embodiment depicted in FIG. 7B, the guiding catheter 610 has been advanced along a guidewire 628 and the ultrasound catheter 654, having an ultrasound device detecting end 652, has been advanced out the distal end of the elongate sheath 610 (i.e., guiding catheter 610) through the pacing catheter exit port 614.

Use of ultrasound in cooperation with targeted placing of a pacing lead 636 in the summit 28 of the left ventricle 26 is previously undisclosed. Likewise, the use of such ultrasound in coordination with a teardrop shaped catheter to assist an operator at a proximal end of the catheter in the determination of the orientation of the distal end of the device, thereby facilitating steering and positioning is previously undisclosed.

II. Methods of Use

Figure 8A:
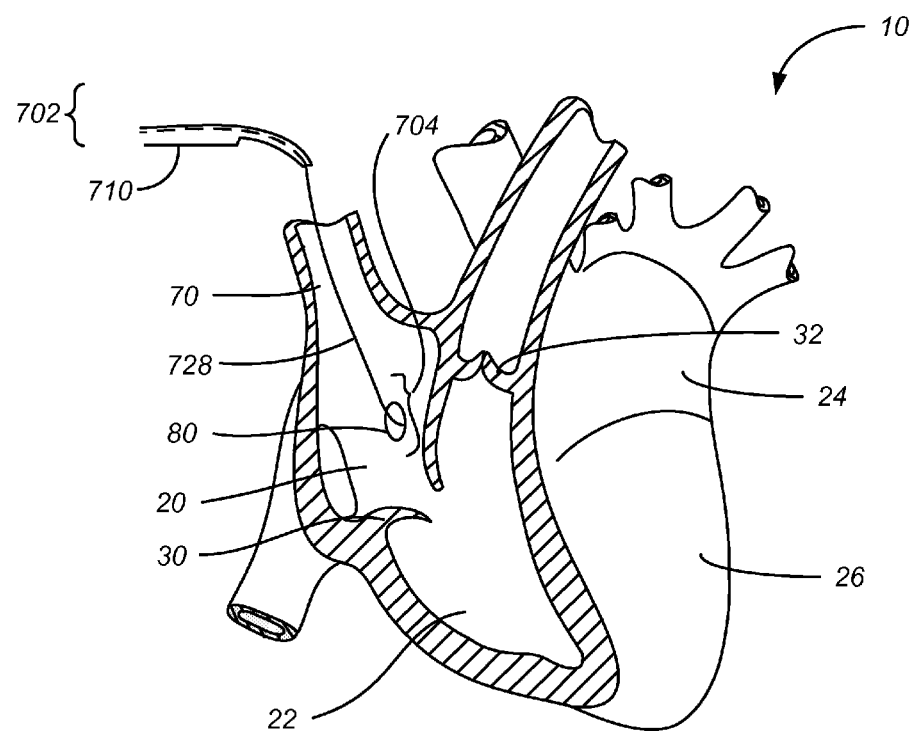
FIG. 8A illustrates a cross-sectional view of a right atrium, a right ventricle, a tricuspid valve, and a pulmonary artery, wherein a guiding catheter is advancing along a guidewire that has been inserted through the superior vena cava, into the right atrium then into coronary sinus.
Figure 8B:
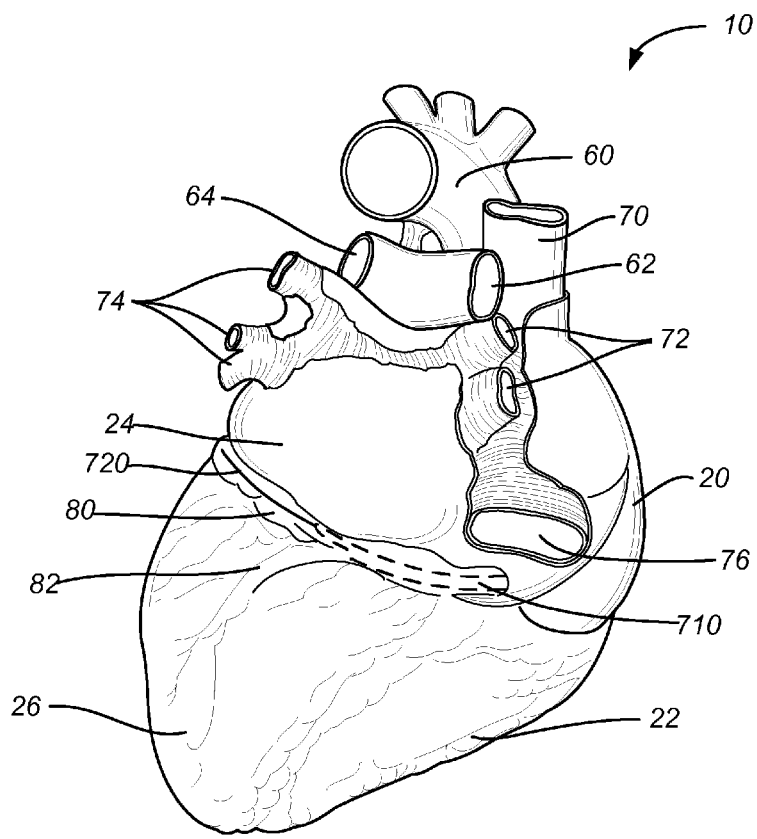
FIG. 8B illustrates a posteroinferior view of a heart wherein a guiding catheter has been advanced along a guidewire and into the coronary sinus.

In FIG. 8A, a cross-sectional view of a heart right atrium 20, right ventricle 22, tricuspid valve 30, and right pulmonary artery 62 is shown. In this depiction, a guiding catheter 710 is shown being advanced along a guidewire 728 which has been inserted through the superior vena cava 710, into the right atrium 20, and then into coronary sinus 80. FIG. 8B depicts a posteroinferior view of heart wherein a guiding catheter 710 embodiment has been advanced along guidewire into coronary sinus 80. Where the device provides radiopaque markers, the markers can be used to determine the location of the distal end of the device relative to the anatomy as the catheter 710 is advanced through the vasculature. Additionally, the cross-sectional shape, e.g., tear drop shape discussed previously, can be viewed to determine the position of, for example, the pacing catheter exit lumen 714 relative to the coronary anatomy so that the electrode can be advanced out of the guiding catheter and optimally positioned at the left ventricular summit.

Figure 8C:
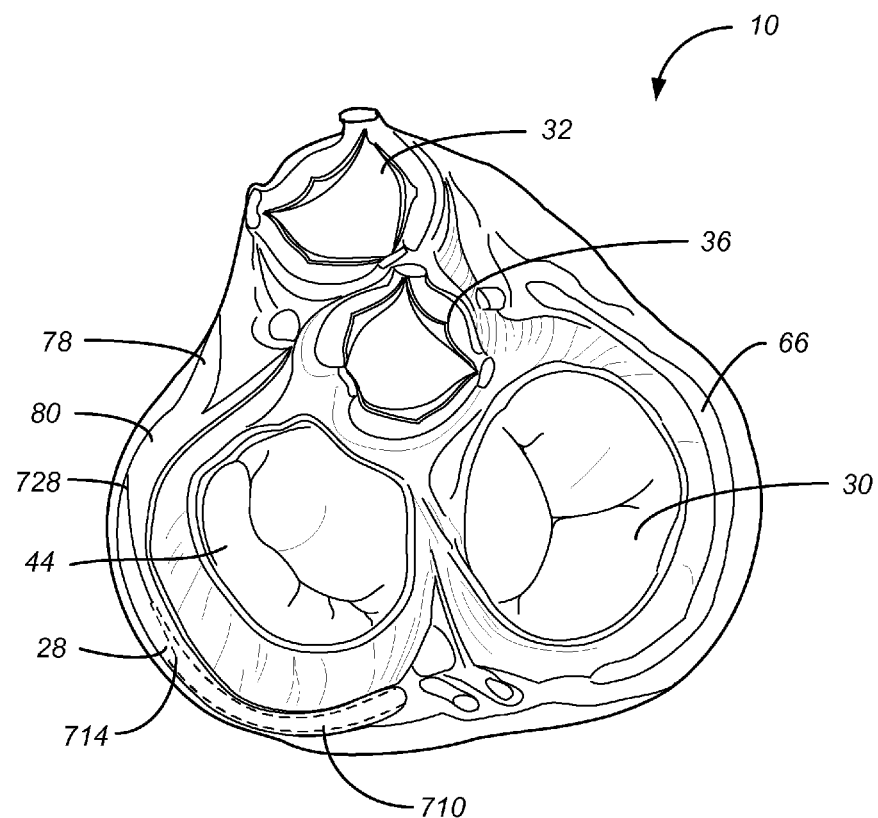
FIG. 8C illustrates a cross-sectional view of a heart in systole wherein a guiding catheter has been advanced along a guidewire into the coronary sinus, and wherein the guiding catheter has been positioned with the pacing catheter distal exit port 68 at about the apex or summit 14 of the left ventricle.
Figure 8D:
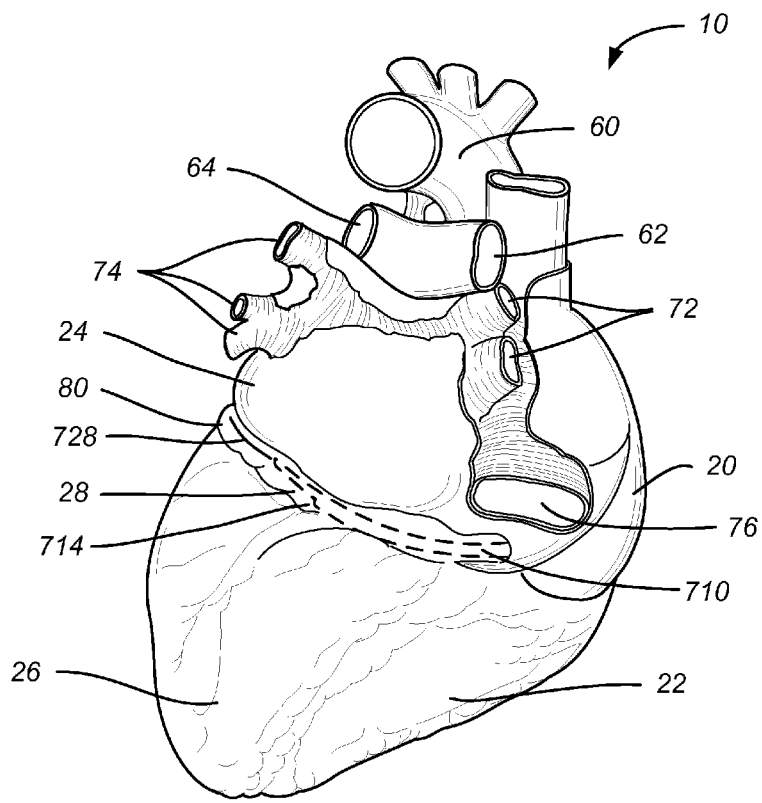
FIG. 8D illustrates a posteroinferior view of a heart in systole wherein a guiding catheter has been advanced along a guidewire into a coronary sinus, wherein the guiding catheter has been positioned with the pacing catheter distal exit port at about the apex or summit of left ventricle.

FIG. 8C depicts a cross-sectional view of heart in systole wherein a guiding catheter 710 embodiment has been advanced along a guidewire 728 into the coronary sinus 80, and wherein the guiding catheter 710 has been positioned with the pacing catheter distal exit port 714 (lumen) at about the apex or summit 28 of left ventricle 26. FIG. 8D shows a posteroinferior view of the same guiding catheter 710 and guidewire 728 placement as shown in FIG. 8C. FIG. 8D depicts a posteroinferior view of heart in systole wherein an embodiment of the guiding catheter 710 has been advanced along a guidewire 728 into coronary sinus 80, wherein the guiding catheter 710 has been positioned with the pacing catheter distal exit port 714 at about the apex or summit 28 of left ventricle 26.

Figure 8E:
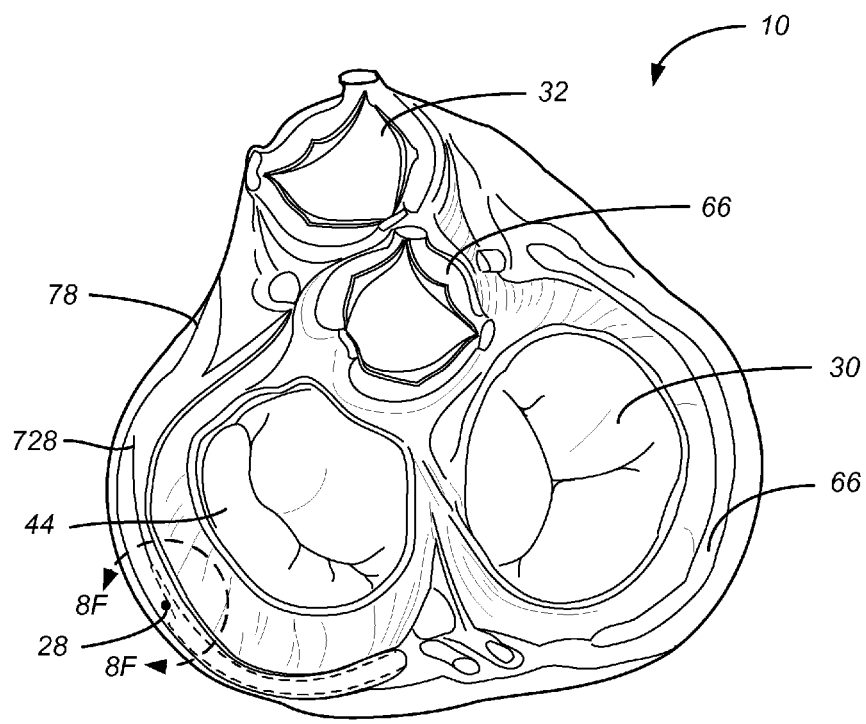
FIG. 8E illustrates a posteroinferior view of a heart in systole wherein a pacing catheter has exited a guiding catheter which has been advanced along a guidewire into the coronary sinus, and wherein the guiding catheter has been positioned with the pacing catheter exit port at apex or summit of left ventricle.
Figure 8F:
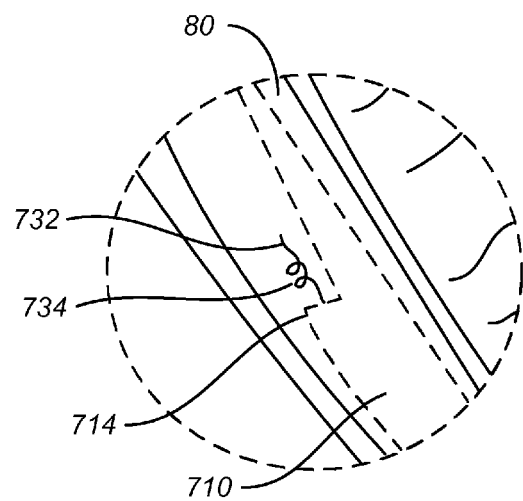
FIG. 8F is a zoomed-in depiction of the LV summit.

FIG. 8E depicts a posteroinferior view of heart in systole wherein an embodiment of a pacing catheter 730 has exited an embodiment of a guiding catheter 710 which has been advanced along a guidewire 728 into coronary sinus 80. In this depiction, the guiding catheter 710 has been positioned with its pacing catheter exit port 714 at apex or summit 28 of left ventricle 26. FIG. 8F also shows a zoomed-in depiction of the LV summit 28 region of the coronary sinus 80 showing the pacing needle electrode 732 and anchor 734 of an embodiment of the pacing catheter 730 exiting the pacing catheter exit port 714 of an embodiment of the guiding catheter 710.

In operation, the sheath of the guiding catheter 710 is placed in standard Seldinger fashion over the guidewire into the coronary sinus 80 and the thin nose 712 portion of the guiding catheter 710 extends into the coronary sinus 80 until it is lodged in the sinus and can be advanced no further. The design locates the more proximal and larger opening 716 in the sheath 710, the one that carries the pacing catheter 730, in approximately the mid-portion of the posterior summit of the left ventricle when the catheter is advanced. Such a position will allow the pacing catheter to be advanced, pierce the coronary sinus 80 and enter the left ventricular summit 14 while the guiding catheter 710 is stably lodged in the coronary sinus 80. In order to accommodate small, medium and large hearts, this sheath 710 may need to be made in several sizes.

The guiding catheter 710 carries this pacing catheter 730 into the coronary sinus 80, where it can be directed, using the radiopaque markers and the cross-sectional shape, to pierce the bottom of the wall of the coronary sinus 80 and enter the summit 14 of the left ventricle 26.

Once the electrode is optimally positioned, at the left ventricular summit and anchored, the sheath is removed and the proximal end of the electrode can be attached to a device for operation. Suitable devices include, for example, ICDs, such as those described in: U.S. Pat. No. 7,203,547 for System and method of implementing a prophylactic pacer/defibrillator; U.S. Pat. No. 7,203,546 for System and method of implementing a prophylactic pacer/defibrillator; U.S. Pat. No. 7,200,434 for Control of arbitrary waveforms for constant delivered energy; U.S. Pat. No. 7,158,825 for Implantable cardioverter defibrillator with leakage detection and prevention system; U.S. Pat. No. 7,151,963 for Control of arbitrary waveforms for constant delivered energy; U.S. Pat. No. 7,103,409 for Atrial and ventricular implantable cardioverter-defibrillator and lead system; U.S. Pat. No. 6,701,187 for Implantable cardiac stimulation device and method for prolonging atrial refractoriness; U.S. Pat. No. 6,675,042 for Defibrillation shock strength determination technology; U.S. Pat. No. 6,633,780 for Cardiac shock electrode system and corresponding implantable defibrillator system; U.S. Pat. No. 6,625,489 for Dynamic non-competitive atrial pacing; U.S. Pat. No. 6,574,505 for Atrial and ventricular implantable cardioverter-defibrillator and lead system; U.S. Pat. No. 6,567,697 for Method and apparatus for electrically forcing cardiac output in an arrhythmia patient; U.S. Pat. No. 6,377,852 for Implanatable cardiac stimulation device and method for prolonging atrial refractoriness; U.S. Pat. No. 6,363,280 for Ventricular synchronized atrial pacing mode of implantable cardioverter/defibrillator; U.S. Pat. No. 6,282,444 for Implantable device with electrical infection control; U.S. Pat. No. 6,275,734 for Efficient generation of sensing signals in an implantable medical device such as a pacemaker or ICD; U.S. Pat. No. 6,094,597 for Implantable medical device incorporating distributed core, step-up transformer; U.S. Pat. No. 6,067,471 for Atrial and ventricular implantable cardioverter-defibrillator and lead system; U.S. Pat. No. 5,957,956 for Implantable cardioverter defibrillator having a smaller mass; U.S. Pat. No. 5,944,746 for ICD with continuous regular testing of defibrillation lead status; U.S. Pat. No. 5,919,213 for Implantable defibrillator system for generating a biphasic waveform with enhanced phase transition.

Figure 9A:
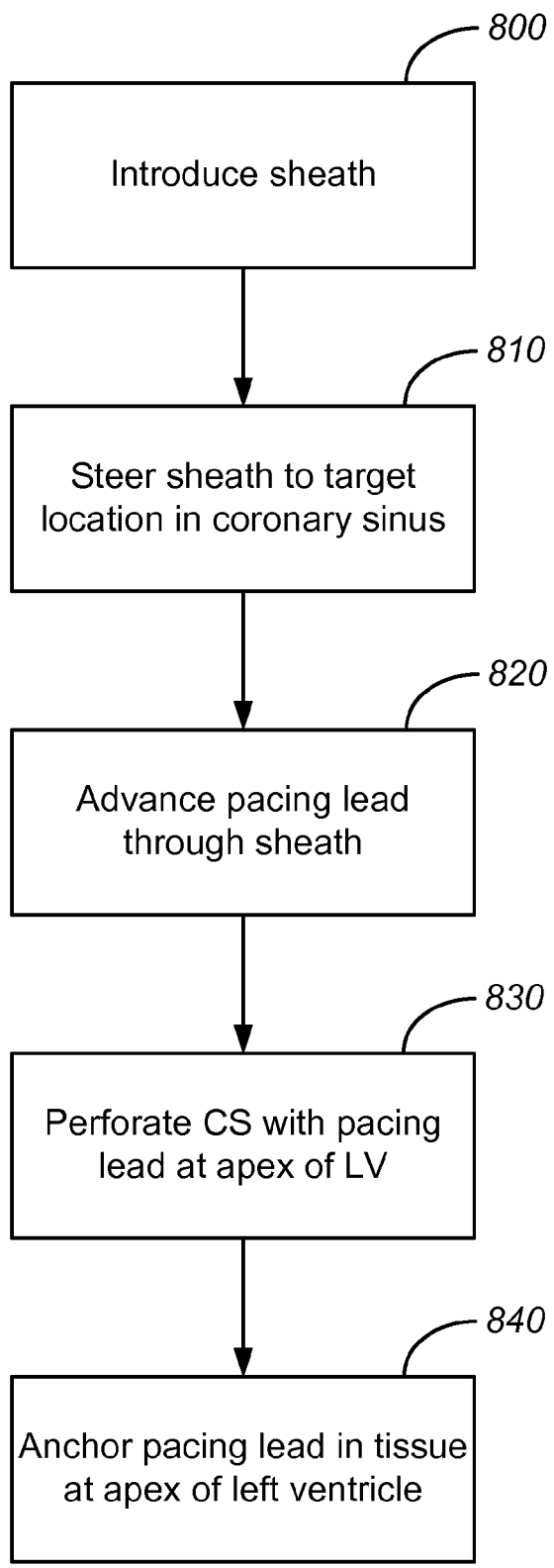
FIG. 9A illustrates a flow chart of a method of use of the system in the coronary anatomy.
Figure 9B:
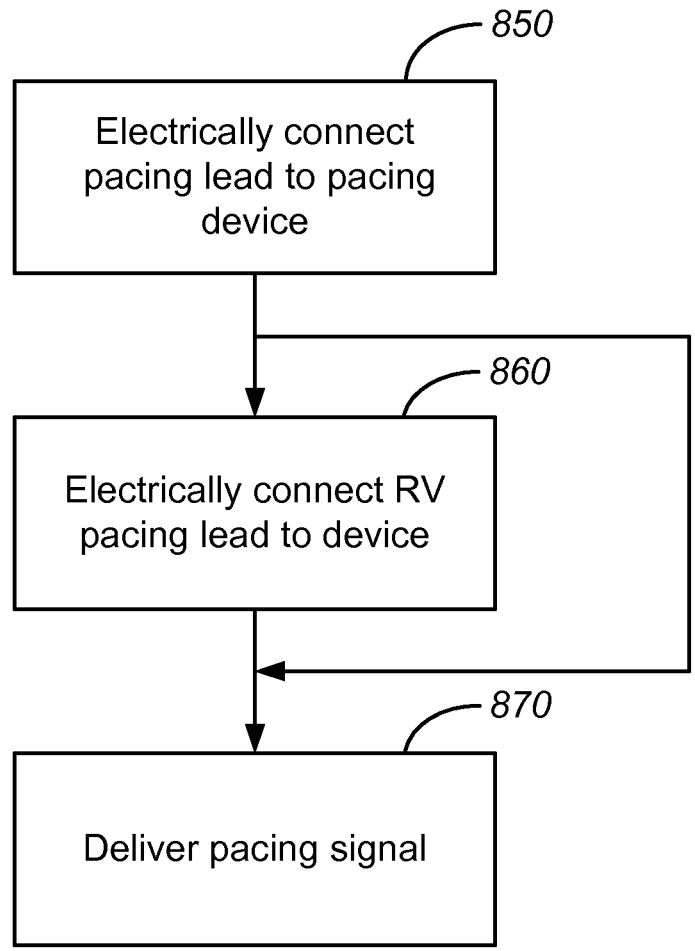
FIG. 9B illustrates a flow chart of a method of use of the system in the coronary anatomy.

FIG. 9A depicts a flow chart of a method of use of the LV summit pacing system (described above) in the coronary anatomy. The method includes the steps of introducing a guiding catheter into the coronary anatomy, steering the sheath to the target location in the coronary sinus, advancing the pacing lead through the sheath, perforating the coronary sinus with the pacing lead at the apex (summit) of the left ventricle, and anchoring the pacing lead in the tissue at the apex (summit) of the left ventricle. FIG. 9B depicts a flow chart of a method of use of the LV summit pacing system in the coronary anatomy, comprising the steps of electrically connecting a pacing lead located at the apex (summit) of the LV to a pacing device, optionally electrically connecting an RV pacing lead (not shown) to the pacing device, and delivering a pacing signal to the LV pacing lead or to both the LV pacing lead and the RV pacing lead (not shown).

III. Kits

The devices disclosed herein can be combined into kits prior to use. The devices would be sterilized and sealed into suitable packaging designed to prevent contamination. A variety of devices and sizes could be provided in each kit in order to facilitate a surgeon's use of the kit in a sterile patient treating setting, such as a hospital operating room, or clinic. Thus, for example, the kit could contain one or more guidewires of different diameters, lengths, and flexibility; one or more elongate sheaths having different diameters, lengths, and distal tip (e.g., nose) configurations; one or more pacing catheters, having different diameters, different lengths, and with or without the pacing needle incorporated; and/or one or more pacing needles having different tip configurations.

Specific configurations and materials for making catheters, electrodes and pacing leads are known in the art. For example, the following patents are directed to catheters suitable for use in the heart: U.S. Pat. No. 7,099,712 for Catheter having multiple spines each having electrical mapping and location sensing capabilities; U.S. Pat. No. 7,097,641 for Catheter with cryogenic and heating ablation; U.S. Pat. No. 7,089,045 for Catheter and method for mapping Purkinje fibers; U.S. Pat. No. 7,081,114 for Electrophysiology/ablation catheter having lariat configuration of variable radius; U.S. Pat. No. 7,047,068 for Microelectrode catheter for mapping and ablation; U.S. Pat. No. 7,041,079 for Occlusion catheter for the ascending aorta; U.S. Pat. No. 7,039,450 for Telescoping catheter; U.S. Pat. No. 6,987,996 for Catheter having mapping assembly; U.S. Pat. No. 6,986,769 for Ablation catheter with cooled linear electrode; U.S. Pat. No. 6,984,232 for Ablation catheter assembly having a virtual electrode comprising portholes; U.S. Pat. No. 6,973,352 for Steerable cardiac pacing and sensing catheter and guidewire for implanting leads; U.S. Pat. No. 6,973,340 for Basket catheter with improved expansion mechanism; U.S. Pat. No. 6,961,602 for Catheter having multiple spines each having electrical mapping and location sensing capabilities; U.S. Pat. No. 6,960,206 for Coiled ablation catheter system; U.S. Pat. No. 6,947,785 for Interface system for endocardial mapping catheter; U.S. Pat. No. 6,926,669 for Heart wall ablation/mapping catheter and method; U.S. Pat. No. 6,916,317 for Tricuspid annular grasp catheter; U.S. Pat. No. 6,902,545 for Multi-channel catheter; U.S. Pat. No. 6,892,091 for Catheter, method and apparatus for generating an electrical map of a chamber of the heart; U.S. Pat. No. 6,839,588 for Electrophysiological cardiac mapping system based on a non-contact non-expandable miniature multi-electrode catheter and method therefor; U.S. Pat. No. 6,837,864 for Multichannel catheter with obturator; U.S. Pat. No. 6,835,188 for Aortic catheter with porous aortic root balloon and methods for inducing cardioplegic arrest; for U.S. Pat. No. 6,830,568 for Guiding catheter system for ablating heart tissue; U.S. Pat. No. 6,826,421 for Endocardial mapping catheter; U.S. Pat. No. 6,821,265 for Multichannel catheter; U.S. Pat. No. 6,807,447 for Triple array defibrillation catheter and method of using the same; U.S. Pat. No. 6,748,255 for Basket catheter with multiple location sensors; U.S. Pat. No. 6,746,431 for Combined catheter system for IABP and determination of thermodilution cardiac output; U.S. Pat. No. 6,741,878 for Basket catheter with improved expansion mechanism; U.S. Pat. No. 6,736,782 for Apparatus, computer program, central venous catheter assembly and method for hemodynamic monitoring; U.S. Pat. No. 6,733,499 for Catheter having circular ablation assembly; U.S. Pat. No. 6,728,563 for Electrophysiology/ablation catheter having "halo" configuration; U.S. Pat. No. 6,723,082 for Delivery catheter system for heart chamber; U.S. Pat. No. 6,723,069 for Electrophysiology positioning catheter; U.S. Pat. No. 7,110,827 for Electrical connectors for medical lead having weld-less wiring connection; U.S. Pat. No. 7,103,409 for Atrial and ventricular implantable cardioverter-defibrillator and lead system; U.S. Pat. No. 7,089,065 for Modified guidewire for left ventricular access lead; U.S. Pat. No. 7,085,606 for Epicardial electrode; U.S. Pat. No. 7,031,773 for Implantable cardiac stimulation system providing autocapture and lead impedance assessment and method; U.S. Pat. No. 7,027,876 for Lead system for providing electrical stimulation to the Bundle of His; U.S. Pat. No. 7,010,358 for Single lead system for high voltage CHF device; U.S. Pat. No. 6,999,821 for Body implantable lead including one or more conductive polymer electrodes and methods for fabricating same; U.S. Pat. No. 6,999,814 for Implantable intravenous cardiac stimulation system with pulse generator housing serving as optional additional electrode; U.S. Pat. No. 6,988,007 for Single pass telescoping cardiac lead for the left heart; U.S. Pat. No. 6,987,999 for Implantable defibrillator with alternating counter electrode; U.S. Pat. No. 6,986,769 for Ablation catheter with cooled linear electrode; U.S. Pat. No. 6,984,232 for Ablation catheter assembly having a virtual electrode comprising portholes; U.S. Pat. No. 6,973,341 for Noninvasive, intrauterine fetal ECG strip electrode; U.S. Pat. No. 6,970,733 for System and method for electrode localization using ultrasound; U.S. Pat. No. 6,968,237 for Implantable coronary sinus lead and lead system; U.S. Pat. No. 6,961,621 for Apparatus and method for stabilizing an implantable lead; U.S. Pat. No. 6,950,696 for Method and circuit for detecting cardiac rhythm abnormalities by analyzing time differences between unipolar signals from a lead with a multi-electrode tip; U.S. Pat. No. 6,944,506 for Stylet feature for resisting perforation of an implantable lead; U.S. Pat. No. 6,934,583 for Implantable lead and method for stimulating the vagus nerve; U.S. Pat. No. 6,909,919 for Cardiac lead incorporating strain gauge for assessing cardiac contractility; U.S. Pat. No. 6,909,916 for Cardiac rhythm management system with arrhythmia classification and electrode selection; U.S. Pat. No. 6,907,297 for Expandable intracardiac return electrode and method of use; U.S. Pat. No. 6,907,296 for Implantable cardiac lead having convenient implant location identification and method of manufacture; U.S. Pat. No. 6,904,315 for Atrial aware VVI: a method for atrial synchronous ventricular (VDD/R) pacing using the subcutaneous electrode array and a standard pacing lead; U.S. Pat. No. 6,901,297 for Stimulation electrode and its use; U.S. Pat. No. 6,901,288 for Sealing assembly for intravenous lead; U.S. Pat. No. 6,889,093 for Electrode lead with multiple branches; U.S. Pat. No. 6,882,886 for Vessel electrode line; U.S. Pat. No. 6,868,291 for Arrangement for implanting an endocardial cardiac lead; U.S. Pat. No. 6,859,667 for Multiplexed medical device lead with standard header; U.S. Pat. No. 6,850,800 for Evoked response detector, averaging the value of the amplitude of the picked-up electrode signal; U.S. Pat. No. 6,849,073 for Apparatus and method for creating, maintaining, and controlling a virtual electrode used for the ablation of tissue; U.S. Pat. No. 6,839,588 for Electrophysiological cardiac mapping system based on a non-contact non-expandable miniature multi-electrode catheter and method therefor; U.S. Pat. No. 6,823,215 for Implantable heart stimulator with microinstability testing for electrode contact with tissue; U.S. Pat. No. 6,804,553 for Bachmann's bundle electrode for atrial defibrillation; U.S. Pat. No. 6,792,318 for Technique for fixating a lead; U.S. Pat. No. 6,792,316 for Cardiac implant cable having a coaxial lead; U.S. Pat. No. 6,788,972 for Implantable cardiac stimulator with electrode-tissue interface characterization; U.S. Pat. No. 6,782,291 for Implantable cardiac stimulation device with automatic evoked response sensing electrode configuration selection and method; U.S. Pat. No. 6,775,566 for Electrode structure and heart rate measuring arrangement.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for implanting a pacing device, comprising the steps of:
    a. introducing a sheath;
    b. steering the sheath to a left ventricular summit;
    c. lodging a distal end of the sheath beyond a posterior summit of a left ventricle;
    d. advancing a pacing lead through a lumen of the sheath to the left ventricular summit;
    e. perforating the coronary sinus with the pacing lead;
    f. coupling the pacing lead to cardiac tissue at the posterior summit of the left ventricular at a first end;
    g. removing the sheath; and
    h. activating the left ventricular summit to achieve early closure of a mitral valve during systole.

2. The method of claim 1, further comprising the steps of:
    i. advancing a right ventricular pacing catheter to a target location within a right ventricle,
    j. positioning the electrode at the target location within the right ventricle.

3. The method of claim 1, further comprising the steps of obtaining an angiogram,
    obtaining a live fluoroscopic image,
    correlating the angiogram with live fluoroscopic image, and
    analyzing the correlated images to identify anatomical structures.

4. The method of claim 1, further comprising the steps of:
    obtaining an angiogram;

obtaining a live intravascular ultrasound;
correlating an angiogram with live intravascular ultrasound; and
analyzing the correlated images to identify anatomical structures.

5. The method of claim 1, comprising the step of using the cross-sectional shape of the device to facilitate steering and perforating.

6. A method for achieving early closure of a mitral valve, comprising the steps of:
 a. introducing a sheath;
 b. steering the sheath to a target location within a coronary sinus;
 c. advancing a left ventricular pacing lead through a lumen of the sheath to the target location within the coronary sinus;
 d. perforating the coronary sinus with the left ventricular pacing lead;
 e. coupling the left ventricular pacing lead to a cardiac stimulation device;
 f. coupling a right ventricular pacing lead from a right ventricle to the cardiac stimulation device;
 g. removing the sheath; and
 h. activating the cardiac stimulation device to deliver energy to the pacing leads to achieve early closure of the mitral valve during systole.

7. The method of claim 6, wherein the step of coupling the right ventricular pacing lead further comprises the step of advancing a right ventricular pacing catheter to a first target location within the heart.

8. The method of claim 7, comprising the step of positioning a right ventricular pacing lead at the first target location within the heart.

9. The method of claim 8, comprising the step of correlating an angiogram with live fluoroscopy.

10. The method of claim 6, comprising the step of correlating an angiogram with live intravascular ultrasound.

11. The method of claim 6, wherein the target location within the coronary sinus is a left ventricular pacing summit.

12. The method of claim 6, comprising the step of using the cross-sectional shape of the device to facilitate the steering and perforating.

\* \* \* \* \*